United States Patent

Sato et al.

[11] Patent Number: 5,380,900
[45] Date of Patent: Jan. 10, 1995

[54] α-METHYLENECYCLOPENTANONE DERIVATIVE AND PROCESS FOR PRODUCING THE SAME

[75] Inventors: Fumie Sato, Fujisawa; Kazutaka Arai; Katsuaki Miyaji, both of Funabashi, all of Japan

[73] Assignee: Nissan Chemical Industries, Limited, Tokyo, Japan

[21] Appl. No.: 834,348

[22] Filed: Feb. 12, 1992

[30] Foreign Application Priority Data

Feb. 26, 1991 [JP] Japan .................................. 3-054019

[51] Int. Cl.$^6$ ............................ C07F 7/08; C07F 7/10; C07F 7/18
[52] U.S. Cl. ..................... 556/436; 556/413; 556/415; 556/423; 556/428; 556/437; 568/325; 568/329; 568/330; 568/42; 568/55; 568/57; 549/416; 549/422; 564/374; 564/462; 558/388; 560/53; 560/121; 560/126
[58] Field of Search ............... 556/436, 413, 415, 423, 556/428, 437; 568/325, 329, 330, 42, 55, 57; 549/416, 422; 564/374, 462; 558/388; 560/53, 121, 126

[56] References Cited

U.S. PATENT DOCUMENTS

| | | | |
|---|---|---|---|
| 4,703,127 | 10/1987 | Rickards et al. | 556/436 X |
| 4,994,619 | 2/1991 | Sato et al. | 564/455 |
| 5,055,592 | 10/1991 | Kolb et al. | 556/436 X |
| 5,136,066 | 8/1992 | Takahashi et al. | 556/436 |
| 5,180,844 | 1/1993 | Takahashi et al. | 556/436 |
| 5,227,505 | 7/1993 | Sato et al. | 556/436 |
| 5,231,208 | 7/1993 | Sato et al. | 556/436 |
| 5,254,708 | 10/1993 | Sato et al. | 556/436 |
| 5,283,349 | 2/1994 | Tanaka et al. | 556/436 |

FOREIGN PATENT DOCUMENTS 2378010 1/1978 France .
4-74152 3/1992 Japan .

OTHER PUBLICATIONS

Toshiharu Yoshino et al., *J. Org. Chem.*, vol. 56 (1991) pp. 3205–3207.
H. Tsujiyama et al., *Tetrahedron Letters*, vol. 31 (1990) pp. 4481–4484.
English Abstract of Japanese Patent Application No. 184487, (1990).
Tetrahedron Letters No. 40, pp. 3899–3902, 1973.
J. Am. Chem. Soc., 97 4745 (1974).
J. Am. Chem. Soc., 97 6260 (1975).
J. Med. Chem., 23 234 (1980).
J. Org. Chem., 43 2102 (1978).
J. Org. Chem., 49 2301 (1984).
J. Org. Chem., 53 1227 (1988).

*Primary Examiner*—Paul F. Shaver
*Attorney, Agent, or Firm*—Birch, Stewart, Kolasch & Birch

[57] ABSTRACT

Disclosed herein is an α-methylene-cyclopentanone derivative represented by the formula [I] below which is useful as an intermediate for pharmaceuticals and insecticides, especially prostaglandins. Also disclosed herein is a process for producing the derivative advantageously on an industrial scale.

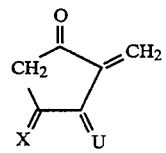

[I]

where X denotes (α-OZ, β-H) or (α-H, β-OZ), with Z representing a protecting group for the hydroxyl group; U denotes (α-H, β-R$^1$) or (β-R$^1$, α-H); R$^1$ denotes

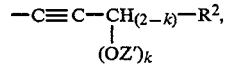

where R$^2$ denotes a protected hydroxyl group, a substituted or unsubstituted C$_{1-15}$ alkyl group, a substituted or unsubstituted C$_{2-15}$ alkenyl group, a substituted or unsubstituted C$_{2-15}$ alkynyl group, or a substituted or unsubstituted C$_{6-15}$ aryl group; Z' denotes a protecting group for the hydroxyl group; and k is 0 or 1).

15 Claims, No Drawings

α-METHYLENECYCLOPENTANONE DERIVATIVE AND PROCESS FOR PRODUCING THE SAME

BACKGROUND OF THE INVENTION

1. Field of the Invention

The present invention relates to an α-methylenecyclopentanone derivative and a process for producing the same. The derivative is useful as an intermediate for the synthesis of pharmaceuticals and insecticides, especially prostaglandins.

2. DESCRIPTION OF THE PRIOR ART

α-methylenecyclopentanone derivatives are now being watched with keen interest because of their usefulness as an intermediate for pharmaceuticals and insecticides. It is especially useful as an intermediate for the synthesis of prostaglandins with high physiological activities.

One of the known processes for the synthesis of prostaglandin represented by the formula (P) is by the conjugate addition reaction. (G. Stark et al., J. Am. Chem. Soc. 97, 4745, 6260 (1975))

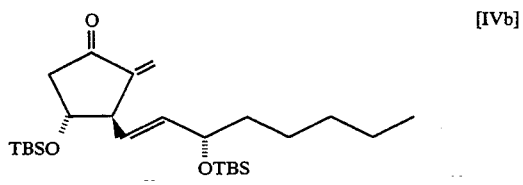

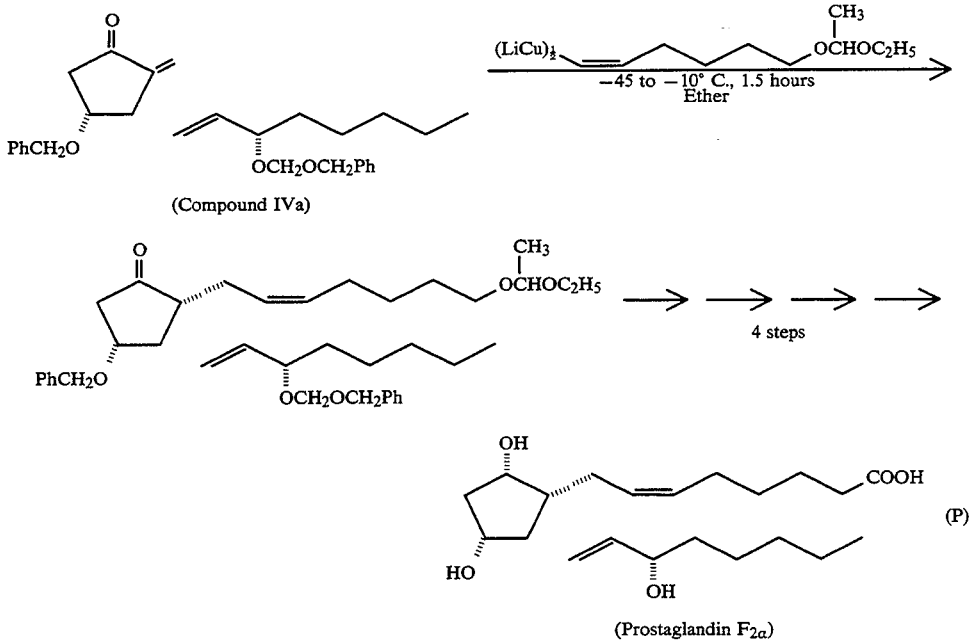

The above-mentioned process is advantageous in that the yield of prostaglandin $F_{2\alpha}$ (P) from the compound [IVa] is high and that it is possible to change the α-chain as desired by selecting an adequate reagent for conjugate addition.

Unfortunately, the known reagent for conjugate addition does not contain a substituent such as $COOR^7$, CN, and $OOCR^8$ (where $R^7$ and $R^8$ denote alkyl groups having 1 to 6 carbon atoms) which readily reacts with an organometallic reagent. Therefore, such a substituent had to be formed by conversion. For example, in the synthesis of the above-mentioned prostaglandin $F_{2\alpha}$ (P), the $CH(CH_3)OC_2H_5$ group is eliminated to form an alcohol which is subsequently oxidized with a chromium-based oxidizing agent (which is toxic) into a carboxylic acid. Such an indirect process poses problems associated with safety and simplicity required for industrial production.

The present inventors proposed in Japanese Patent Application No. 184487/1990 a process for producing prostaglandins advantageously on an industrial scale which have the substituent incapable of direct introduction by the conventional process as mentioned above, using a reagent for conjugate addition which permits the direct introduction of such a substituent. This process comprises performing conjugate addition reaction on an α-methylenecyclopentanone derivative represented by the formula [IVb] below and an organozinc reagent represented by the formula [V] below in the presence of cuprous cyanide and trialkylsilyl chloride, followed by optional hydrolysis. The reaction product is a prostaglandin precursor having $COOR^7$, CN, or $OOCR^8$ as the substituent of the α-chain.

[IVb]

(TBS=SiMe₂ᵗBu, Me denoting a methyl group and ᵗBu denoting a butyl group)

$$Zn(CH_2)_l W_m (CH_2)_n Z^1 \qquad [V]$$

(where W denotes a group selected from $CH_2CH_2$, CH=CH, and C≡C; l denotes an integer of 1 to 7; m and n each denote an integer of 0 to 5; $Z^1$ denotes $COOR^7$,

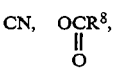

hydrogen atom, chlorine atom, or a substituted or unsubstituted aromatic group; $R^7$ and $R^8$ each denote an alkyl group having 1 to 6 carbon atoms; and Zn denotes zinc.)

The above-mentioned G. Stark's process is disadvantageous in that the yield of the compound [IVa] is low, the reagent used for synthesis is expensive, and the compound [IVa] is usually of racemic modification but is not an optically active substance. (ibid.; D. R. Morton et al., J. Org. Chem., 43, 2102 (1978); and A. B. Kodivsky et al., J. Org. Chem., 49, 2301 (1984)).

Thus, the present inventors proposed in Japanese Patent Laid-Open No. 128/1990 (U.S. Ser. No. 207,549, EP 88.305442.1, Hungary 3090/88) a new process for producing prostaglandin intermediates [IVa] and [IVb] in high yields on an industrial scale. This process comprises performing conjugate addition reaction on an α-aminomethylcyclopentenone derivative represented by the formula (II) below and an organometallic reagent. Therefore, this process permits an optically active substance to be produced easily in high yields from an inexpensive raw material.

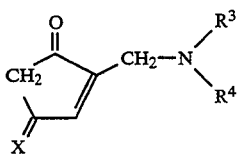

[II]

(where X denotes (α-OZ, β-H) or (α-H, β-OZ), with Z representing a protecting group for the hydroxyl group; and $R^3$ and $R^4$, which are the same or different, each denote a substituted or unsubstituted alkyl group or phenyl group having 1 to 10 carbon atoms.)

On the other hand, 13-dehydroprostaglandins are known well for their high physiological activity. (J. Fleed et al., J. Med. Chem., 23, 234 (1980)) They are conventionally synthesized by (1) the ring opening reaction of epoxide (J. Fleed et al., Tetrahedron Lett., 3899 (1973)), or (2) the dehydrohalogenation of 14-halogen-substituted-prostaglandins. (Shibasaki et al., J. Org. Chem., 53, 1227 (1988)).

SUMMARY OF THE INVENTION

It is an object of the present invention to provide an α-methylenecyclopentanone derivative useful as an intermediate for pharmaceuticals, especially prostaglandins. It is another object of the present invention to provide a process for producing said derivative.

To achieve the above-mentioned objects, the present inventors carried out a series of researches, which led to the finding that a new α-methylenecyclopentanone derivative represented by the formula [I] below can be synthesized efficiently in a short process without using a toxic reagent by the reaction between an α-aminomethylcyclopentenone derivative represented by the formula [II] below and an organoaluminum compound represented by the formula [III] below, and that the derivative is useful as an intermediate for pharmaceuticals and insecticides, especially prostaglandins, particularly 13-dehydroprostaglandins. The present invention is based on this finding.

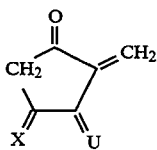

[I]

(wherein X denotes (α-OZ, β-H) or (α-H, β-OZ), with Z representing a protecting group for the hydroxyl group; and U denotes (α-H, β-$R^1$) or (β-$R^1$, α-H).

$R^1$ denotes

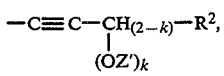

where $R^2$ denotes a protected hydroxyl group, a substituted or unsubstituted $C_{1-15}$ alkyl group, a substituted or unsubstituted $C_{2-15}$ alkenyl group, a substituted or unsubstituted $C_{2-15}$ alkynyl group, or a substituted or unsubstituted $C_{6-15}$ aryl group; Z' denotes a protecting group for the hydroxyl group; and k is 0 or 1.)

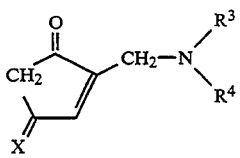

[II]

(where X denotes (α-OZ, β-H) or (α-H, β-OZ), with Z representing a protecting group for the hydroxyl group; and $R^3$ and $R^4$ which are the same or different, each denote a substituted or unsubstituted alkyl group or phenyl group having 1 to 10 carbon atoms.)

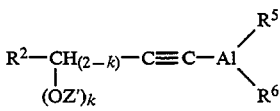

[III]

(where $R^2$, Z', and k are as defined above; $R^5$ and $R^6$, which are the same or different, each denote an alkyl group having 1 to 10 carbon atoms.)

DESCRIPTION OF THE PREFERRED EMBODIMENTS

The new α-methylenecyclopentanone derivative of the invention is represented by the formula [I] below.

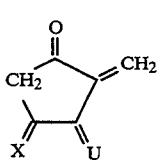

[I]

where X denotes (α-OZ, β-H) or (α-. H, β-OZ), with Z representing a protecting group for the hydroxyl group. Examples of Z include arylmethyl groups (such as benzyl group, and p-methoxybenzyl group), trialkylsilyl groups (such as trimethylsilyl group and t-butyldimethylsilyl group), alkoxyalkyl groups (such as methoxymethyl group), aralkyloxyalkyl groups (such as benzyloxymethyl group), trityl group, and tetrahydropyranyl (THP) group. U denotes (α-H, β-$R^1$) or (β-$R^1$, α-H), with $R^1$ being represented by the formula [M] below.

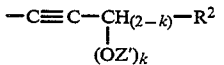

[M]

where $R^2$ denotes a protected hydroxyl group, substituted or unsubstituted $C_{1-15}$ group, substituted or unsubstituted $C_{2-15}$ alkenyl group, substituted or unsubstituted $C_{2-15}$ alkynyl group, and substituted or unsubstituted $C_{6-15}$ aryl group. Examples of these groups include methyl group, ethyl group, n-propyl group, i-propyl group, n-butyl group, i-butyl group, t-butyl group, amyl group, hexyl group, heptyl group, octyl group, nonyl group, decyl group, 2-methylhexyl group, 2-hexyl group, cyclopentyl group, cyclohexyl group, cyclohexylmethyl group, hexa-4-in-2-yl group, hept-4-in-2-yl group, 2,6-dimethyl-hept-5-en-1-yl group, pent-1-en-1-yl group, pent-2-en-1-yl group, hex-1-en-2-yl group, 3-ethoxy-2-methyl-propan-2-yl group, ethoxyethyl group, 5-methoxyhexyl group, 2-(trimethylsilyloxy)-2-hexyl group, halogenated methyl group, halogenated n-butyl group, halogenated n-pentyl group, halogenated nonyl group, phenyl group, benzyl group, halogenated phenyl group, n-pentyloxymethyl group, 1-ethoxy-2-methyl-propan-2-yl group, phenoxymethyl group, benzyloxymethyl group, p-chlorophenoxymethyl group, 2-phenylethyl group, benzyloxyethyl group, p-fluorophenoxymethyl group, phenyl-acetylenyl group, m-chlorophenoxymethyl group, m-trifluoromethylphenoxymethyl group, 1-butyl-cyclopropyl group, 3-ethyl-cyclopentyl group, benzothiophenon-5-yl group, 2-octenyl group, 3-methoxycarbonylpropyl group, and vinyl group. $Z'$ denotes a protecting group for the hydroxyl group. It is exemplified by those groups enumerated for the above-mentioned Z. The subscript k is 0 or 1.

According to the present invention, the α-methylenecyclopentanone derivative represented by the formula [I] above can be produced by reaction between an α-aminomethylcyclopentenone derivative represented by the formula [II] below and an organoaluminum compound represented by the formula [III] below.

The first starting material (α-aminomethylcyclopentenone derivative represented by the formula [II] below) is a known compound. It can be easily prepared by the process disclosed in Japanese Patent Laid-Open No. 128/1990.

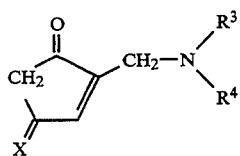

[II]

where X denotes (α-OZ, β-H) or (α-H, β-OZ), with Z being a protecting group for the hydroxyl group as defined above; and $R^3$ and $R^4$, which may be the same or different, each denote a substituted or unsubstituted $C_{1-10}$ (preferably $C_{1-5}$) alkyl group or phenyl group, including alkyl groups (such as methyl group, ethyl group, n-propyl group, and i-propyl group), substituted alkyl groups (such as benzyl group and p-chlorobenzyl group), phenyl group, and substituted phenyl groups (such as p-chlorophenyl group).

The second starting material is an organoaluminum compound represented by the formula [III] below.

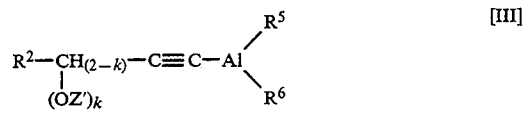

[III]

where $R^2$ is as defined above; $R^5$ and $R^6$, which may be the same or different, each denote a $C_{1-10}$ alkyl group (such as methyl group, ethyl group, n-butyl group, n-octyl group, and i-propyl group); and $Z'$ and k are as defined above.

This organoaluminum compound can be prepared by various processes. It can be advantageously produced by the process proposed by the present inventors (Sato et al., Tetrahedron Lett., 30 7083 (1989)). The process consists of the following steps.

First, an acetylene compound represented by the formula [VI] below is reacted with an alkyl lithium (such as n-butyl lithium) for lithiation, and the reaction product is further reacted with an alkyl aluminum halide represented by the formula [VI] below.

[VI]

(where $R^2$, $Z'$ and k are as defined above.)

[VII]

(where X denotes a halogen atom and $R^5$ and $R^6$ are as defined above.)

The lithiation of the acetylene compound [VI] should preferably be carried out by using the alkyl lithium in an amount of 0.6 to 1.1 equivalents, especially 0.8 to 1 equivalents, for the acetylene compound in the presence of a solvent. Any solvent can be used so long as it does not interfere with the reaction. It includes, for example, tetrahydrofuran, hexane, pentane, benzene, toluene, and diethyl ether. They may be used alone or in combination with one another. The lithiation should be carried out at a temperature from $-40°$ to $60°$ C., preferably from $-20°$ to $30°$ C., depending on the freezing point and boiling point of the solvent used.

The alkyl aluminum halide [VII], which includes dimethyl aluminum chloride, diethyl aluminum chloride, and diisobutyl aluminum chloride, should be used in an amount of 0.8 to 1.2 equivalents, preferably 0.9 to 1.05 equivalents, for the acetylene compound. This reaction should be carried out in the presence of a solvent as in the case of lithiation, and the reaction temperature ranges from $-40°$ to $60°$ C., especially from $-20°$ to $30°$ C., depending on the freezing point and boiling point of the solvent used. The reaction temperature should preferably be set rather low in consideration of the reaction heat which is generated when the reactant is added and then set rather high to complete the reaction after the reactant has been added.

According to the present invention, the α-methylenecyclopentanone derivative [I'] is obtained by reaction between the α-aminocyclopentenone derivative [II'] and the organoaluminum compound [III']. The reaction is represented by the equation A below.

Reaction schema A

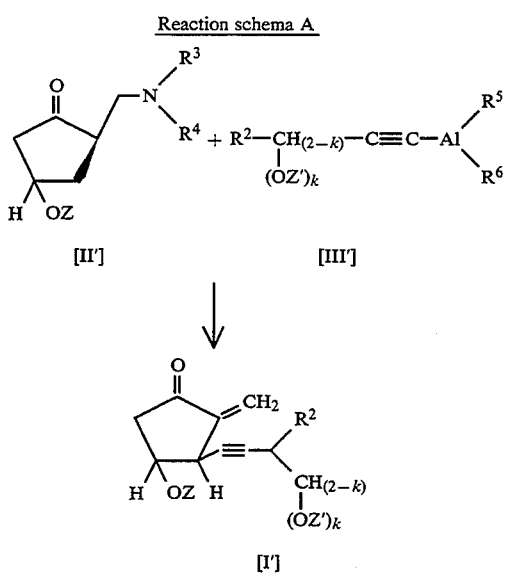

In this reaction, it is desirable to use the organoaluminum compound in an amount of 0.5 to 4 equivalents, preferably 0.8 to 2 equivalents, for the α-aminomethylcyclopentenone derivative. The reaction should preferably be carried out in a solvent. Any solvent can be used so long as it does not interfere with the reaction. It includes, for example, tetrahydrofuran, hexane, pentane, benzene, toluene, and diethyl ether. The reaction temperature should be in the range from −20 to 60° C., preferably from 10° to 60' C., depending on the freezing point and boiling point of the solvent used. It is possible to prepare the organoaluminum compound [III] and to carry out this reaction in a series of operations. In this case, it is desirable to use a common solvent for both reactions.

The foregoing reaction gives rise to the α-methylenecyclopentanone derivative [I] which is a mixture of transisomers (in which the substituent at the 4-position is trans with respect to the substituent at the 3-position as indicated by the formulas [Ia] and [Id] below) and cisisomers (in which the substituent at the 4-position is cis with respect to the substituent at the 3-position as indicated by the formula [Ib] and [Ic] below). In this mixture, the trans-isomers are dominant over the cis-isomers, and they can be easily separated from each other on account of their greatly different polarity. Separation may be accomplished in the usual way, e.g., by column chromatography. Thus, the process of the present invention is favorable to the production of an intermediate [Ia] for 13-dehydroprostaglandins.

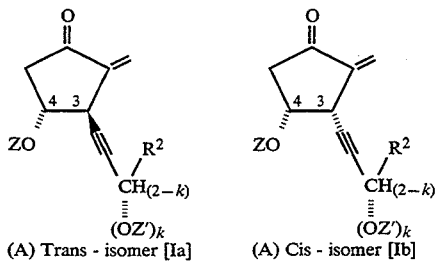

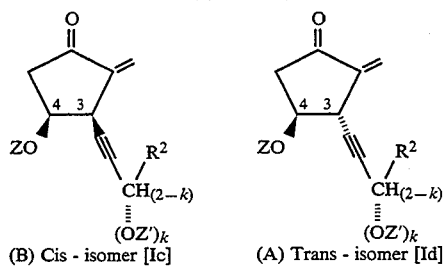

(where $R^2$, Z, and Z' are as defined above.)

Incidentally, the compound [Ia] can be converted into 13-dehydroprostaglandins by the present inventors' process (Japanese Patent Application No. 184487/1990) mentioned above.

The present invention provides an α-methylenecyclopentanone derivative of the formula [I] above, which is useful as an intermediate for pharmaceuticals, especially prostaglandins. According to the process of the present invention, it is possible to prepare the α-methylenecyclopentanone derivative [I], such as the one represented by the formula [I a] below, efficiently in high yields on an industrial scale without using a toxic reagent.

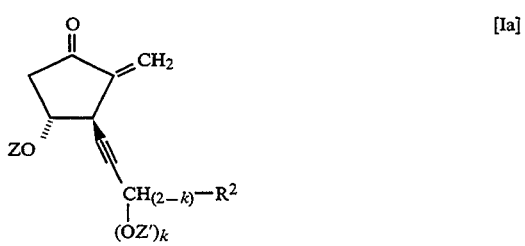

(where Z, Z', $R^2$, and k are as defined above.)

EXAMPLES

The invention will be described in more detail with reference to the following examples, which are not intended to restrict the scope of the invention. Abbreviations used in the examples are given below.

THF for tetrahydrofuran, Me for methyl group, Et for ethyl group, n-Bu for n-butyl group, t-Bu for t-butyl group, TBS for t-BuMe$_2$Si group, TMS for Me$_2$Si group, and pyr for pyridine. NMR was measured using solutions in deuterated chloroform (CDCl$_3$).

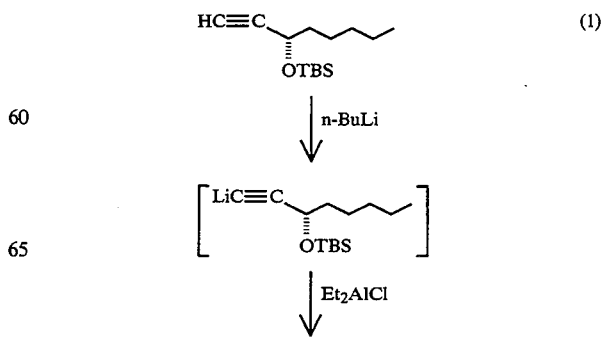

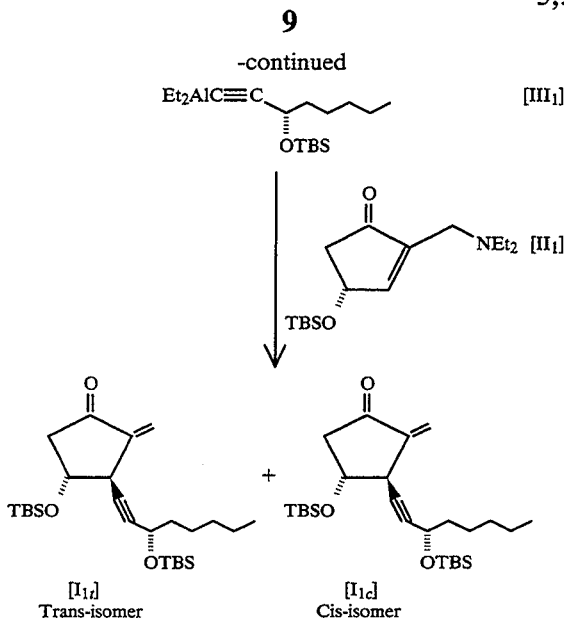

[III₁]

[II₁]

[I₁ₜ] Trans-isomer

[I₁c] Cis-isomer

In 9 ml of benzene was dissolved 1.08 g (4.5 mmol) of 3-(t-butyldimethylsilyloxy)-1-octene (1). To the solution cooled with ice water was added 3.9 mmol of n-butyl lithium in 2.35 ml of hexane solution (1.66M), followed by stirring for 30 minutes. To the mixed solution cooled with ice water was added 4.5 mmol of diethyl aluminum chloride in 4.64 ml of hexane solution (0.97M), followed by stirring. Thus there was obtained an organoaluminum compound [III].

To the organoaluminum compound [III] kept at room temperature was added 889 mg (3.0 mmol) of (R)-2-[(diethylamino)methyl]-4-[(t-butyldimethylsilyl)oxy]-2-cyclopentenone [II] dissolved in 15 ml of benzene, followed by stirring for 15 minutes. The reaction solution was added dropwise with stirring to a mixture of saturated aqueous solution of ammonium chloride, 3N hydrochloric acid, and hexane. The organic layer was separated, and the aqueous layer was extracted with hexane and the extract was combined with the former. The organic layer was washed with saturated aqueous solution of sodium bicarbonate and then dried with anhydrous magnesium sulfate. The solution was concentrated under reduced pressure to give an oily substance. Upon purification by silica gel column chromatography, there was obtained an α-methylenecyclopentanone derivative composed of 1.14 g (82% yield) of trans-isomer [I] and 0.19 g (14% yield) of cis-isomer [I]. Physical properties of these compounds are shown below.

Examples 2 to 6

A variety of α-methylenecyclopentanone derivatives [I] were prepared by reacting (R)-2-[(diethylamino)methyl]-4-[(t-butyl -dimethylsilyl)oxy]-2-cyclopentenone [II] with a variety of organoaluminum reagents [III] shown in Tables 1 and 2 in the same manner as in Example 1. The results of Examples 1 to 7 are shown in Tables 1 and 2. The physical properties of the resulting compounds are shown below. Incidentally, in Tables 1 and 2 the subscript 11, 12 attached to J and C denotes the numbering of prostaglandins.

TABLE 1

| | | | Analysis of reaction product (Compound [I]) | | | | |
| | | | | Yield (%) | | Coupling constant for ¹H-NMR | |
| Example | Compound [III] used for reaction | Compound obtained | Compound [Iₜ] | Compound [Ic] | Compound [Iₜ] | Compound [Ic] | |
|---|---|---|---|---|---|---|---|
| 1 | Et₂AlC≡C—CH(OTBS)—(CH₂)₄CH₃ | [III₁] | [I₁ₜ] [I₁c] | 82 | 14 | 6.8 | 4.0 |
| 2 | Et₂Al—C≡C—CH(OTBS)—cyclohexyl | [III₂] | [I₂ₜ] [I₂c] | 90 | 4 | 6.8 | 4.2 |
| 3 | Et₂Al—C≡C—CH(OTBS)—(CH₂)₄CH₃ | [III₃] | [I₃ₜ] [I₃c] | 83 | 8 | 6.8 | 4.8 |
| 4 | Et₂Al—C≡C—C(OTMS)(CH₃)—(CH₂)₃CH₃ | [III₄] | [I₄ₜ] [I₄c] | 50 | 19 | 7.0 | 4.0 |
| 5 | Et₂Al—C≡C—CH₂—CH(CH₃)—CH₂—OTBS | [III₅] | [I₅ₜ] [I₅c] | 54 | 45 | 6.8 | 4.0 |
| 6 | Et₂Al—C≡C—(CH₂)₄CH₃ | [III₆] | [I₆ₜ] [I₆c] | 59 | 39 | 7.2 | 3.8 |

Analysis of reaction product (Compound [I])

¹³C NMR Shift of

TABLE 1-continued

| Example | Compound [III] used for reaction | | C-11 and C-12 (ppm) Compound [I_d] (C-11/C-12) | Compound [I_c] (C-11/C-12) | $[\alpha]_D^{25}$ (C, CHCl$_3$) Compound [I_d] (CHCl$_3$) |
|---|---|---|---|---|---|
| 1 | Et$_2$AlC≡C—CH(OTBS)—C$_6$H$_{13}$ | [III$_1$] | 73.3/43.6 | 69.5/42.1 | −54.6° (C 1.03) |
| 2 | Et$_2$Al—C≡C—CH(OTBS)—C$_6$H$_{11}$ | [III$_2$] | 73.3/43.6 | 69.6/42.3 | −50.0° (C 1.20) |
| 3 | Et$_2$Al—C≡C—CH(OTBS)—C$_5$H$_{11}$ | [III$_3$] | 73.3/43.5 | 69.6/42.3 | −51.2° (C 1.38) |
| 4 | Et$_2$Al—C≡C—CH$_2$—C(CH$_3$)(OTMS)—C$_5$H$_{11}$ | [III$_4$] | 73.5/43.8 | 69.8/42.4 | — |
| 5 | Et$_2$Al—C≡C—CH$_2$OTBS | [III$_5$] | 73.2/43.5 | 69.6/42.1 | −30.0° (C 1.12) |
| 6 | Et$_2$Al—C≡C—C$_6$H$_{13}$ | [III$_6$] | 73.7/43.8 | 69.9/42.5 | −45.1° (C 1.50) |

[I$_{1d}$]

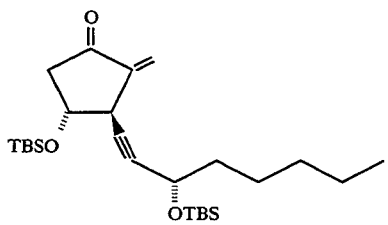

$^1$H NMR (200 MHz) δ0.08, 0.09 and 0.12 (3s, 12H), 0.81–0.99 (m, 3H), 0.89 (s, 18H), 1.15–1.73 (m, 8H), 2.32 (dd, J=7.6, 18.0 Hz, 1H), 2.71 (dd, J=6.6, 18.0 Hz, 1H), 3.47–3.61 (m, 1H), 4.19–4.33 (m, 1H), 4.37 (dt, J=1.6, 6.4 Hz, 1H), 5.55 (d, J=2.8 Hz, 1H), 6.13 (d, J=3.0 Hz, 1H) $^{13}$C NMR (50 MHz) δ−5.1, −4.9, −4.8, −4.6, 13.9, 17.9, 18.1, 22.5, 24.9, 25.6, 25.7, 31.4, 38.8, 43.6 (C-12, PG numbering), 46.9, 63.1, 73.3 (C-11), 81.7, 86.5, 119.9, 145.1, 201.9 IR (neat) 2930, 2860, 1740, 1645, 1465, 1255, 1120, 840, 780 cm$^{-1}$ R$_f$ 0.60 (hexane/ET$_2$O=6/1) $[\alpha]_D^{25}$ −54.6° (c 1.03, CHCl$_3$)

[I$_{1c}$]

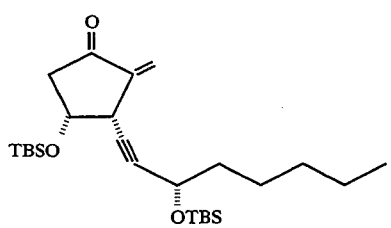

$^1$H NMR (200 MHz) δ0.08, 0.09 and 0.11 (3s, 12H), 0.08, 0.09 and 0.11 (3s, 12H), 0.79–1.02 (m, 3H), 0.85 and 0.90 (2s, 18H), 1.17–1.74 (m, 8H), 2.37 (dd, J=2.4, 17.8 Hz, 1H, 2.46 (dd, J=4.0, 17.8 Hz, 1H), 3.64–3.71 (m, 1H, 4.38 (dt, J=2.0, 6.4 Hz, 1H), 4.47–4.57 (m, 1H), 5.58 (d, J=2.8 Hz, 1H), 6.17 (d, J=3.2 Hz, 1H) $^{13}$C NMR (50 MHz) δ−5.4, −5.1, −4.9, −4.7, 13.8, 17.9, 18.0, 22.4, 24.8, 25.5, 25.6, 31.3, 38.7, 42.1 (C-12), 47.3, 63.0, 69.5 (C-11), 80.2, 87.0, 119.2, 143.9, 202.7 IR (neat) 2930, 2850, 1730, 1640, 1465, 1250, 1070, 835, 770 cm$^{-1}$ R$_f$ 0.38 (hexane/ET$_2$O=6/1)

[I$_{2d}$]

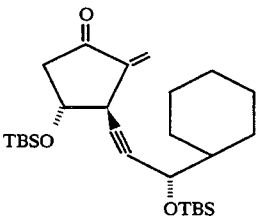

$^1$H NMR (200 MHz) δ0.07, 0.08 and 0.12 (3s, 12H), 0.88 (s, 18H), 0.92–1.92 (m, 11H), 2.32 (dd, J=7.4, 17.8 Hz, 1H), 2.71 (dd, J=6.5, 17.8 Hz, 1H), 3.48–3.58 (m, 1H), 4.11 (dd, J=1.4, 6.2 Hz, 1H), 4.20–4.32 (m, 1H), 5.55 (d, 2.6 Hz, 1H), 6.13 (d, J=3.0 Hz, 1H) $^{13}$C NMR (50 MHz) δ−5.3, −4.94, −4.88, −4.6, 17.9, 18.1, 25.6, 25.7, 25.89, 25.91, 26.4, 28.5, 28.6, 43.6 (C-12), 44.9, 46.9, 67.8, 73.3 (C-11), 82.4, 85.5, 119.8, 145.1, 201.9 IR (neat) 2930, 2850, 1735, 1640, 1470, 1380, 1255, 1105, 830, 770 cm$^{-1}$ R$_f$ 0.60 (hexane/ET$_2$O=6/1) $[\alpha]_D^{25}$ −50.0° (c 1.20, CHCl$_3$)

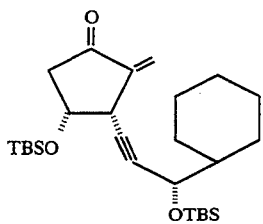
[I₂c]

¹H NMR (200 MHz) δ0.07, 0.09 and 0.10 (3s, 12H), 0.85 and 0.90 (2s, 18H), 0.95–1.95 (m, 11H), 2.30–2.55 (m, 2H), 3.64–3.76 (m, 1H), 4.11 (dd, J=1.9, 6.3 Hz, 1H), 4.45–4.57 (m, 1H), 5.58 (dd, J=0.8, 2.8 Hz, 1H), 6.17 (d, J=3.2 Hz, 1H) ¹³C NMR (50 MHz) δ−5.3, −5.0, −4.8, −4.5, 18.0, 18.1, 25.7, 25.8, 26.1, 26.4, 28.5, 28.7, 42.3 (C-12), 44.9, 47.5, 67.9, 69.6 (C-11), 80.9, 86.3, 119.6, 144.0, 203.2 IR (neat) 2930, 2850, 1730, 1645, 1460, 1380, 1240, 1090, 830, 770 cm⁻¹ R_f 0.34 (hexane/ET₂O=6/1)

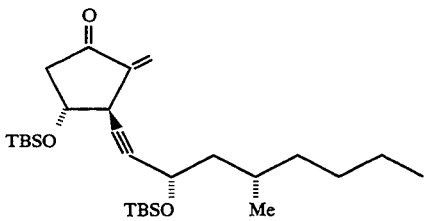
[I₃t]

¹H (200 MHz) δ0.09, 0.10 and 0.12 (3s, 12H), 0.89 (s, 18H), 0.80–0.99 (m, 6H), 1.00–1.72 (m, 9H), 2.32 (dd, J=7.4, 18.0 Hz, 1H), 2.71 (dd, J=6.6, 18.0 Hz, 1H), 3.47–3.56 (m, 1H), 4.15–4.33 (m, 1H), 4.44 (dt, J=1.6, 7.0 Hz, 1H), 5.54 (d, J=2.6 Hz, 1H), 6.13 (d, J=3.0 Hz, 1H) ¹³C NMR (50 MHz) δ−5.1, −4.9, −4.8, −4.5, 14.0, 17.9, 18.1, 19.8, 22.9, 25.6, 25.7, 29.0, 29.3, 36.4, 43.5 (C-12), 46.2, 46.9, 61.7, 73.3 (C-11), 82.0, 86.4, 120.0, 145.0, 202.1 IR (neat)

2930, 2850, 1740, 1640, 1460, 1360, 1250, 1120, 1080, 835, 770 cm⁻¹ R_f 0.60 (hexane/ET₂O=6/1) [α]_D²⁵ −51.2° (c 1.38, CHCl₃)

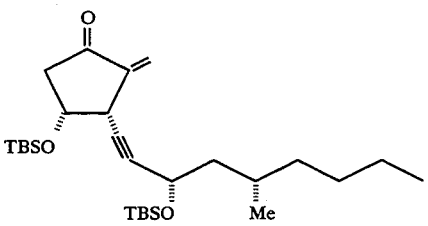
[I₃c]

¹H NMR (200 MHz) δ0.08, 0.09. 0.10 and 0.12 (4s, 12H), 0.85 and 0.89 (2s, 18H), 0.75–1.01 (m, 6H), 1.02–1.78 (m, 9H), 2.37 (dd, J=2.6, 17.9 Hz, 1H), 2.46 (dd, J=3.4, 17.9 Hz, 1H), 3.64–3.71 (m, 1H), 4.46 (dt, J=1.8, 6.8 Hz, 1H), 4.46–4.55 (m, 1H), 5.58 (d, J=2.8 Hz, 1H), 6.17 (d, J=3.2 Hz, 1H) ¹³C NMR (50 MHz) δ−5.2, −5.0, −4.8, −4.5, 14.0, 18.0, 18.1, 19.8, 22.9, 25.6, 25.7, 29.6, 29.9, 36.3, 42.3 (C-12), 46.2, 47.4, 61.7, 69.6 (C-11), 80.4, 87.2, 119.6, 143.9, 203.2 IR (neat) 2930, 2850, 1730, 1640, 1460, 1360, 1255, 1070, 840, 780 cm⁻¹ R_f 0.38 (hexane/ET₂O=6/1)

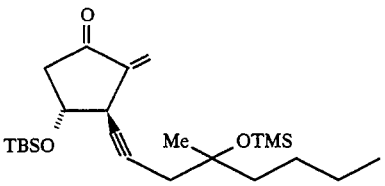
[I₄t]

¹H NMR (200 MHz) δ0.09 and 0.12 (2s, 15H), 0.88 (s, 9H), 0.80–0.96 (m, 3H), 1.15–1.62 (m, 6H), 1.27 (s, 3H), 2.20–2.45 (m, 1H), 2.36 (d, J=2.0 Hz, 2H), 2.69 (dd, J=6.6, 17.8 Hz, 1H), 3.48 (dt, J=7.0, 2.4 Hz, 1H), 4.18–4.30 (m, 1H), 5.52 (d, J=2.4 Hz, 1H), 6.11 (d, J=3.6 Hz, 1H) ¹³C NMR (50 MHz) δ−5.0, −4.9, 2.4, 14.0, 17.9, 23.0, 25.6, 25.9, 27.4, 32.9, 41.4, 43.8 (C-12), 46.8, 73.5 (C-11), 75.5, 79.7, 82.3, 119.5, 145.6, 202.0 IR (neat) 2940, 2860, 1740, 1640, 1460, 1370, 1240, 1120, 840 cm⁻¹ R_f 0.58 (hexane/ET₂O=6/1)

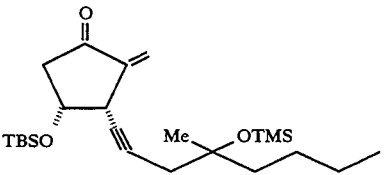
[I₄c]

¹H NMR (200 MHz) δ0.06, 0.08 and 0.10 (3s, 15H), 0.79–0.98 (m, 3H), 0.84 (s, 9H), 1.18–1.80 (m, 6H), 1.30 and 1.31 (2s, 3H), 2.22–2.52 (m, 4H), 3.57–3.67 (m, 1H), 4.46–4.54 (m, 1H), 5.56 (d, J=2.6 Hz, 1H), 6.15 (d, J=3.2 Hz, 1H) ¹³C NMR (50 MHz) δ−5.0, −4.9, 2.4, 14.0, 18.0, 23.0, 25.6, 25.9, 27.4, 33.2, 41.4, 41.5, 42.4 (C-12), 47.5, 69.8 (C-11), 75.6, 78.3, 83.0, 119.4, 144.5, 203.4 IR (neat) 2930, 2860, 1730, 1650, 1470, 1380, 1240, 1160, 1100, 1070, 840 cm⁻¹ R_f 0.40 (hexane/ET₂O=6/1)

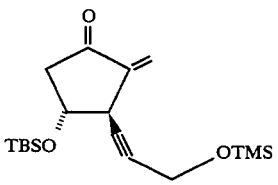
[I₅t]

¹H NMR (200 MHz) δ0.08, 0.09 and 0.11 (3s, 12H), 0.87 and 0.88 (2s, 18H), 2.31 (dd, J=7.6, 18.0 Hz, 1H), 2.69 (dd, J=6.6, 18.0 Hz, 1H), 3.46–3.57 (m, 1H), 4.17–4.33 (m, 1H), 4.34 (d, J=2.0 Hz, 2H), 5.54 (d, J=2.2 Hz, 1H), 6.12 (d, J=3.6 Hz, 1H) ¹³C NMR (50 MHz) δ−5.3, −5.1, −4.8, 17.9, 18.1, 25.6, 25.7, 43.5 (C-12), 46.8, 51.7, 73.2 (C-11), 82.7, 83.0, 119.9, 144.7, 201.7 IR (neat) 2940, 2860, 1730, 1640, 1460, 1365, 1245, 1080, 830, 770 cm⁻¹ R_f 0.50 (hexane/ET₂O=6/1) [α]_D²⁵ −30.3° (c 1.12, CHCl₃)

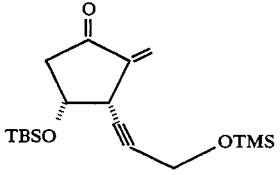
[I₅c]

¹H NMR (200 MHz) δ0.06, 0.08 and 0.10 (3s, 12H), 0.83 and 0.89 (2s, 18H), 2.35 (dd, J=2.2, 17.5 Hz, 1H), 2.45 (dd, J=3.6, 17.5 Hz, 1H), 3.62-3.72 (m, 1H), 4.35 (d, J=2.0 Hz, 2H), 4.48-4.57 (m, 1H), 5.58 (d, J=2.8 Hz, 1H), 6.16 (d, J=3.4 Hz, 1H) ¹³C NMR (50 MHz) δ−5.4, −5.1, −4.9, 18.0, 18.1, 25.5, 25.7, 42.1 (C-12), 47.4, 51.8, 69.6 (C-11), 81.5, 83.6, 119.6, 143.6, 202.9 IR (neat) 2930, 2850, 1730, 1645, 1460, 1360, 1250, 1080, 830, 770 cm⁻¹ R_f 0.26 (hexane/ET₂O=6/1)

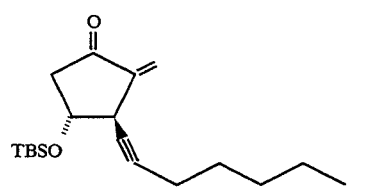

[I_6t]

¹H (200 MHz) δ0.10 and 0.13 (2s, 6H), 0.76-1.00 (m, 3H), 0.89 (s, 9H), 1.13-1.75 (m, 6H), 2.20 (dt, J=2.2, 7.0 Hz, 2H), 2.31 (dd, J=8.0, 17.8 Hz, 1H), 2.69 (dd, J=6.6, 17.8 Hz, 1H), 3.46 (dt, J=7.2, 2.2 Hz, 1H), 4.16-4.29 (m, 1H), 5.53 (dd, J=0.8, 3.0 Hz, 1H), 6.12 (dd, J=0.8, 3.2 Hz, 1H) ¹³C NMR (50 MHz) δ−5.0, −4.8, 13.8, 18.0, 18.6, 22.1, 25.6, 28.4, 31.0, 43.8 (C-12), 46.8, 73.7 (C-11), 78.0, 85.0, 119.4, 145.7, 202.1 IR (neat) 2930, 2860, 1735, 1640, 1470, 1385, 1260, 1220, 1120, 840, 780 cm⁻¹ R_f 0.53 (hexane/ET₂O=6/1) [α]_D²⁵ 45.1° (c 1.50, CHCl₃)

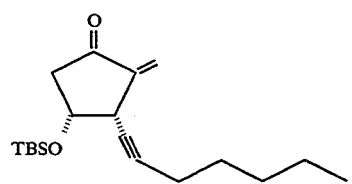

[I_6c]

¹H NMR (200 MHz) δ0.08 and 0.10 (2s, 6H), 0.75-0.95 (m, 3H), 0.85 (s, 9H), 1.10-1.70 (m, 6H), 2.22 (dt, J=2.2, 7.0 Hz, 2H), 2.36 (dd, J=2.2, 17.8 Hz, 1H), 2.45 (dd, J=3.4, 17.8 Hz, 1H), 3.60 (dt, J=3.8, 2.2 Hz, 1H), 4.46-4.55 (m, 1H) 5.58 (dd, J=1.0, 3.0 Hz, 1H), 6.17 (d, J=3.4 Hz, 1H) ¹³C NMR (50 MHz) δ−5.0, −4.9, 13.9, 18.1, 18.8, 22.1, 25.6, 28.5, 31.1, 42.5 (C-12), 47.6, 69.9 (C-11), 76.2, 85.7, 119.6, 144.5, 203.7 IR (neat) 2920, 2850, 1730, 1640, 1460, 1390, 1250, 1100, 1060, 930, 830, 770 cm⁻¹ R_f 0.37 (hexane/ET₂O=6/1)

Example 7

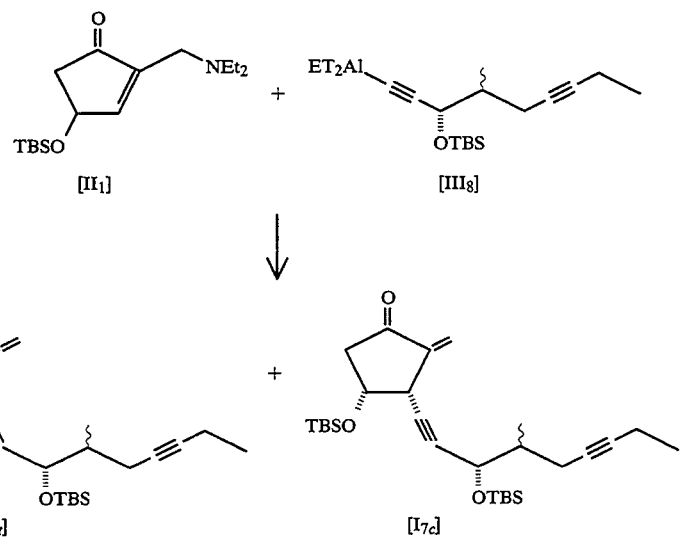

The reaction shown above was carried out in the same manner as in Example 1 to give α-methylenecyclopentanone derivatives [I], [I] shown above, Their physical properties are shown below.

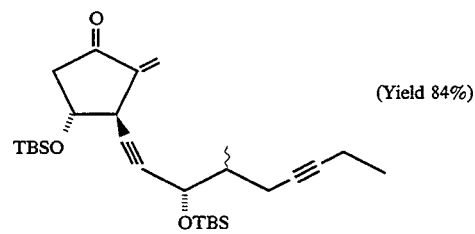

[I_7t]

(Yield 84%)

¹H NMR (CDCl₃, 300 MHz) δ0.09 0.10 and 0.12 (3s, 12H), 0.88 (s, 18H), 1.02 and 1.03 (2d, J=6.8 Hz and J=6.8 Hz, 3H), 1.10 (t, J=7.3 Hz, 3H), 1.73-1.91 (m, 1H), 2.00-2.39 (m, 4H), 2.32 (dd, J=7.4, 17.9 Hz, 1H), 2.70 (dd, J=17.9, 6.4 Hz, 1H), 3.53 (d, J=6.5 Hz, 1H), 4.21-4.30 (m, 1H), 4.37 and 4.47 (2d, J=6.32 Hz and J=4.1 Hz, 1H) 5.54 (d, J=2.7 Hz, 1H), 6.13 (d, J=3.0 Hz, 1H) ¹³C NMR (CDCl₃, 75 MHz) δ−5.1, −4.7, −4.6, −4.4, 12.5, 14.4, 14.7, 15.2, 18.0, 18.2, 22.0, 22.1, 25.7, 25.8, 40.1, 40.4, 43.6, 47.0, 65.4, 66.3, 73.2, 77.3, 77.9, 82.6, 82.8, 82.9, 83.1, 84.6, 85.1, 119.7, 144.8, 201.3 R_f 0.57 (hexane/Et₂O=6/1, SiO₂) IR (neat) 2960, 2934, 2862, 2364, 1738,1649, 1473, 1363, 1255, 1123, 1079, 837, 777 cm⁻¹ [α]_D²⁵ −30.3° (c 2.51 CHCl₃)

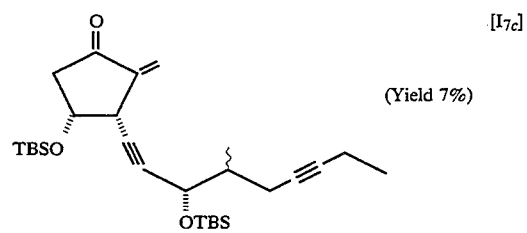

[I_7c]

(Yield 7%)

¹H NMR (CDCl₃, 300 MHz) δ0.06 and 0.08 (2s, 12H), 0.84 and 0.88 (2s, 18H), 1.04 (d, J=6.8 Hz, 3H), 1.09 (t, J=7.4 Hz, 3H), 1.48–2.72 (m, 7H), 3.67 (d, J=2.2 Hz, 1H), 4.32–4.55 (m, 2H), 5.56 (d, J=2.9 Hz, 1H), 6.15 (brs, 1H) $^{13}$C NMR (CDCl$_3$, 75 MHz) δ−5.2, −4.8, −4.59, −4.34, 12.4, 14.4, 14.7, 15.3, 18.1, 18.2, 22.0, 22.2, 25.7, 25.8, 40.1, 40.5, 42.3, 47.4, 65.4, 66.3, 69.5, 69.6, 77.3, 77.8, 81.0, 81.4, 82.8, 83.0, 85.4, 85.9, 119.4, 143.7, 202.4 R$_f$0.34 (hexane/Et$_2$O=6/1, SiO$_2$) IR (neat) 2960, 2932, 2862, 2364, 1738, 1649, 1464, 1363, 1257, 1098, 1069, 940, 839, 777 cm$^{-1}$ Example 8 to 14

The α-methylenecyclopentanone derivatives [I$_i$] shown below was the given in the same manner as in Example 1.

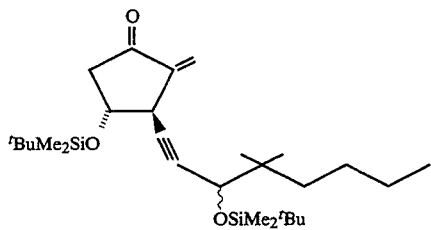
[I$_{8d}$]

$^1$H NMR (CDCl$_3$, 200 MHz) δ0.07, 0.10, 0.11 and 0.13 (4s, 12H) 0.70–1.10 (m, 27H), 1.10–1.70 (m, 6H), 2.32 (dd, J=7.0, 17.9 Hz, 1H), 2.72 (dd, J=6.4, 17.9 Hz, 1H), 3.49–3.59 (m, 1H), 4.055 and 4.047 (2d, J=1.58 Hz and J=1.76 Hz, 1H), 4.21–4.34 1H), 5.55 and 5.56 (2d, J=2.4 Hz and J=2.6 Hz, 1H), 6.15 (d, J=3.0 Hz, 1H)

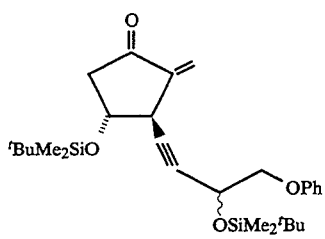
[I$_{9d}$]

$^1$H NMR (CDCl$_3$, 200 MHz) δ0.11, 0.12, 0.14 and 0.15 (4s, 12H), 0.90 and 0.91 (2s, 18H), 2.33 (dd, J=7.7, 18.0 Hz, 1H), 2.71 (dd, J=6.6, 28.0 Hz, 1H), 3.50–3.60 (m, 1H), 4.02–4.08 (m, 2H), 4.20–4.38 (m, 1H), 4.70–4.83 (m, 1H), 5.5 (d, J=2.6 Hz, 1H), 6.15 (d, J=3.1 Hz, 1H), 6.82–7.01 (m, 3H), 7.17–7.3 (m, 2H)

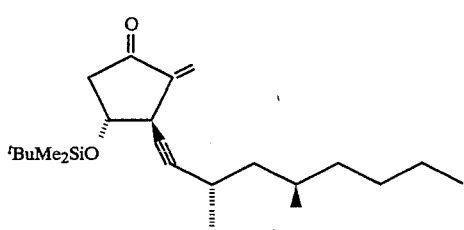
[I$_{10d}$]

$^1$H NMR (CDCl$_3$, 300 MHz) δ0.03–0.15 (m, 12H), 0.80–0.93 (m, 24H), 1.06–1.80 (m, 9H), 2.33 (dd, J=7.4, 17.9 Hz, 1H), 2.71 (dd, J=6.4, 17.9 Hz, 1H), 3.41–3.56 (m, 1H), 4.20–4.32 (m, 1H), 4.44 (t, J=6.59 Hz, 1H), 5.55 (br.s, 1H), 6.14 (br.s, 1H) IR (neat) 2920, 2850, 2210, 1730, 1630, 1450, 1360, 1240, 1100, 1080, 820, 760 cm$^{-1}$

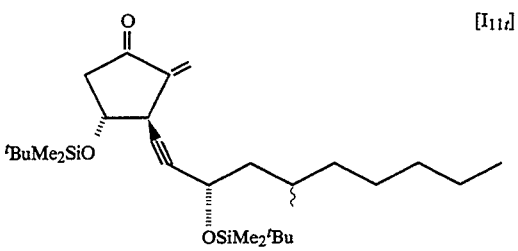
[I$_{11d}$]

$^1$H NMR (CDCl$_3$, 300 MHz) δ0.10, and 0.13 (2s, 12H), 0.80–1.05 (m, 24H), 1.06–1.80 (m, 11H), 2.33 (dd, J=7.4, 18.1Hz, 1H), 2.71 (dd, J=6.3, 18.1 Hz, 1H), 3.43–3.66 (m, 1H), 4.20–4.35 (m, 1H), 4.45 (t, J=6.5 Hz, 1H), 5.55 (brs, 1H), 6.14 (brs, 1H) IR (neat) 2920, 2850, 2330, 1730, 1630, 1460, 1360, 1240, 1110, 1080, 830 770 cm$^{-1}$

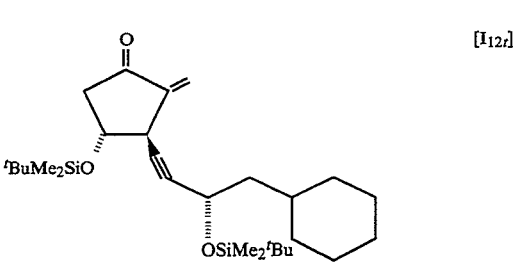
[I$_{12d}$]

$^1$H NMR (CDCl$_3$, 300 MHz) δ0.07–0.14 (m, 12H), 0.89 (s, 18H), 1.03–1.80 (m, 13H), 2.33 (dd, J=7.4, 17.9 Hz, 1H), 2.71 (dd, J=6.4, 17.9 Hz, 1H), 3.41–3.54 (m, 1H), 4.22–4.32 (m, 1H), 4.47 (t, J=6.8 Hz, 1H), 5.55 (d, J=2.5 Hz, 1H), 6.14 (d, J=2.7 Hz, 1H) IR (neat) 2930, 2850, 1735, 1640, 1460, 1360, 1250, 1220, 1100, 1000, 940 830, 770 cm$^{-1}$

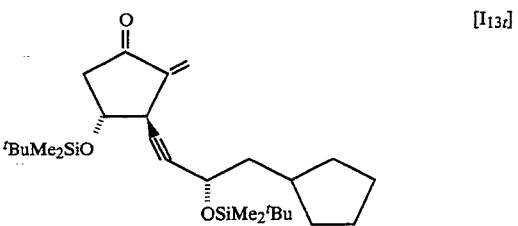
[I$_{13d}$]

$^1$H NMR (CDCl$_3$, 300 MHz) δ0.07–0.17 (m, 12H), 0.89 (s, 18H), 1.03–2.02 (m, 11H), 2.33 (dd, J=7.6, 17.9 Hz, 1H), 2.71 (dd, J=6.4, 17.9 Hz, 1H), 3.41–3.58 (m, 1H), 4.22–4.31 (m, 1H), 4.39 (t, J=6.7 Hz, 1H), 5.55 (d, J=2.4 Hz, 1H), 6.14 (d, J=3.0 Hz, 1H) IR (neat) 2930, 2850, 1735, 1638, 1460, 1360, 1245, 1220, 1100, 1000, 935 825, 770 cm$^{-1}$

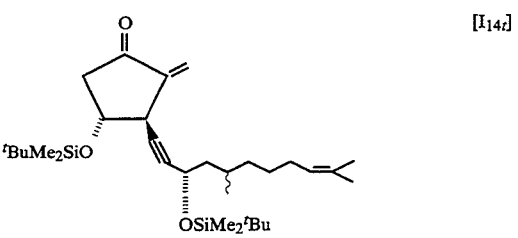
[I$_{14d}$]

$^1$H NMR (CDCl$_3$, 300 MHz) δ0.10 and 0.13 (2s, 12H), 0.80–1.02 (m, 21H), 1.05–1.82 (m, 5H), 1.60 (s, 3H), 1.67

(s, 3H), 1.90–2.06 (m, 2H), 2.33 (dd, J=7.4, 17.8 Hz, 1H), 2.71 (dd, J=6.4, 17.8 Hz, 1H), 3.49–3.57 (m, 1H), 4.22–4.37 (m, 1H), 4.45 (t, J=5.9 Hz, 1H), 5.08 (t, J=6.1 Hz, 1H), 5.55 (d, J=1.8 Hz, 1H), 6.14 (d, J=2.5 Hz, 1H)

Referential Example

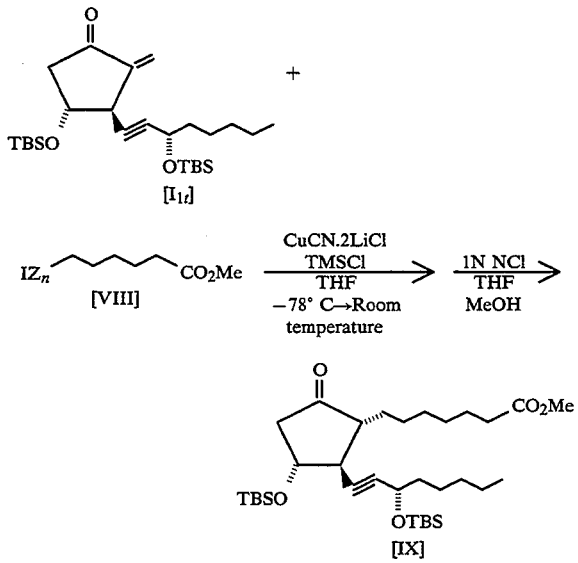

To 0.5 ml of THF solution (1.6M) containing 0.8 mmol of iodo[5-methoxycarbonylpentyl] zinc (II) of the formula [VIII] was added dropwise 1.1 ml of THF solution (0.88M) containing 0.96 mmol of CuCN.2LiCl at −78° C., followed by stirring for 10 minutes. To the mixture were further added dropwise 186 mg (0.4 mmol) of α-methylenecyclopentanone derivative of formula [I$_{1t}$] and 2 ml of diethyl ether solution containing 0.09 ml (0.72 mmol) of trimethylsilyl chloride at −78° C. The temperature of the reactants was gradually raised to room temperature over 3 hours. The mixture was stirred for 8 hours at room temperature. To the mixture was added 10 ml of saturated aqueous solution of NH$_4$Cl and then extracted twice with hexane (8 ml each). The resulting organic layer was dried with MgSO$_4$, filtered, and concentrated under reduced pressure. To the concentrate were added 1.5 ml of methanol, 1.5 ml of THF, and 1.5 ml of 1N hydrochloric acid at 0° C., followed by stirring for 10 minutes. The solution was extracted with hexane. After separation, the organic layer was washed with 10 ml of saturated aqueous solution of NaHCO$_3$ and then with 5 ml of saturated aqueous solution of NaCl. Upon filtration and concentration under reduced pressure, there was obtained a crude product (about 300 mg). This product was purified by silica column chromatography to give 205 mg (0.34 mmol) of the compound [IX] in 80 % yield. Its analytical values are shown below.

$^1$H NMR (200 MHz) δ0.07, 0.08 and 0.10 (3s, 12H), 0.78–0.92 (m, 3H), 0.87 and 0.88 (2s, 18H), 1.15–1.78 (m, 18H), 2.05–2.25 (m, 1H), 2.14 (dd, J=7.4, 18.0 Hz, 1H), 2.28 (t, J=7.2 Hz, 2H), 2.55–2.70 (m, 1H), 2.65 (dd, J=6.8, 18.0 Hz, 1H), 3.64 (s, 3H), 4.20–4.34 (m, 1H), 4.33 (dt, J=1.6, 6.5 Hz, 1H) $^{13}$C NMR (50 MHz) δ−5.2, −5.1, −4.9, −4.7, 13.8, 17.8, 18.1, 22.5, 24.8, 24.9, 25.6, 25.7, 26.6, 28.8, 28.9, 29.2, 31.3, 33.9, 38.7, 42.2, 47.2, 51.3, 54.9, 63.0, 73.5, 83.8, 84.9, 174.4, 215.6 IR (neat) 2940, 2860, 1740, 1465, 1365, 1255, 1090, 830, 770 cm$^{-1}$ [α]$_D^{25}$ −47.3° (c 1.96, CHCl$_3$)

What is claimed is:

1. An α-methylenecyclopentanone derivative represented by the formula [I]

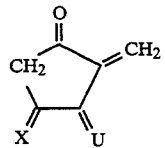

wherein X denotes (α-OZ, β-H) or (β-H, β-OZ), with Z representing a hydroxyl protecting group; U denotes (α-H, β-R$^1$) or (β-R$^1$, α-H); R$^1$ denotes

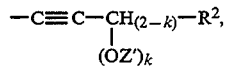

wherein R$^2$ denotes a protected hydroxyl group, a substituted or unsubstituted C$_{1-15}$ alkyl group, a substituted or unsubstituted C$_{2-15}$ alkenyl group, a substituted or unsubstituted C$_{2-15}$ alkynyl group, or a substituted or unsubstituted C$_{6-15}$ aryl group; Z′ denotes a hydroxyl protecting group; and k is 0 or 1.

2. A process for producing the α-methylenecyclopentanone derivative defined in claim 1, which comprises reacting an α-aminomethylcyclopentenone derivative represented by the formula [II] with an organoaluminum compound represented by the formula [III]:

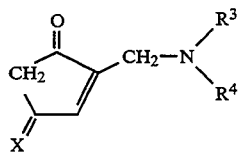

where X denotes (α-OZ, β-H) or (α-H, β-OZ), with Z representing a hydroxyl protecting group; and R$^3$ and R$^4$, which are the same or different, each denote a substituted or unsubstituted alkyl group or phenyl group having 1 to 10 carbon atoms;

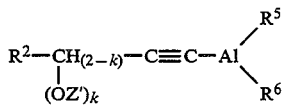

where R$^2$ denotes a protected hydroxyl group, a substituted or unsubstituted C$_{1-15}$ alkyl group, a substituted or unsubstituted C$_{2-15}$ alkenyl group, a substituted or unsubstituted C$_{2-15}$ alkynyl group, or a substituted or unsubstituted C$_{6-15}$ aryl group; R$^5$ and R$^6$ which are the same or different, each denote an alkyl group having 1 to 10 carbon atoms, Z′ denotes a hydroxyl protecting group; and k is 0 or 1.

3. The derivative according to claim 1, wherein Z and Z′ are each independently a group selected from the group consisting of arylmethyl groups, trialkylsilyl groups, alkoxyalkyl groups, aralkyloxyalkyl groups, trityl group, and tetrahydropyranyl group, butyldimethylsilyl group, a methoxymethyl group, a benzyloxymethyl group, a trityl group, and a tetrahydropyranyl group.

4. The derivative according to claim 3, wherein Z and Z' each independently represent a t-butyldimethylsilyl group or a trimethylsilyl group.

5. The derivative according to claim 1, wherein R² is selected from the group consisting of a methyl group, ethyl group, n-propyl group, i-propyl group, n-butyl group, i-butyl group, t-butyl group, amyl group, hexyl group, heptyl group, octyl group, nonyl group, decyl group, 2-methylhexyl group, 2-hexyl group, cyclopentyl group, cyclohexyl group, cyclohexylmethyl group, hexa-4-in-2-yl group, hept-4-in-2-yl group, 2,6-dimethyl-hept-5-en-1-yl group, pent-1-en-1-yl group, pent-2-en-1-yl group, hex-1-en-2-yl group, 3-ethoxy-2-methyl-propan-2-yl group, ethoxyethyl group, 5-methoxyhexyl group, 2-(trimethylsilyloxy)-2-hexyl group, halogenated methyl group, halogenated n-butyl group, halogenated n-pentyl group, halogenated nonyl group, phenyl group, benzyl group, halogenated phenyl group, n-pentyloxymethyl group, 1-ethoxy-2-methyl-propan-2-yl group, phenoxymethyl group, benzyloxymethyl group, p-chlorophenoxy methyl group, 2-phenylethyl group, benzyloxyethyl group, p-fluorophenoxymethyl group, phenylacetylenyl group, m-chlorophenoxymethyl group, m-trifluoromethylphenoxymethyl group, 1-butyl-cyclopropyl group, 3-ethyl-cyclopentyl group, benzothiophenon-5-yl group, 2-octenyl group, 3-methoxycarbonylpropyl group, and vinyl group.

6. The derivative according to claim 3, wherein R² is selected from the group consisting of a methyl group, ethyl group, n-propyl group, i-propyl group, n-butyl group, i-butyl group, t-butyl group, amyl group, hexyl group, heptyl group, octyl group, nonyl group, decyl group, 2-methylhexyl group, 2-hexyl group, cyclopentyl group, cyclohexyl group, cyclohexylmethyl group, hexa-4-in-2-yl group, hept-4-in-2-yl group, 2,6-dimethyl-hept-5-en-1-yl group, pent-1-en-1-yl group, pent-2-en-1-yl group, hex-1-en-2-yl group, 3-ethoxy-2-methyl-propan-2-yl group, ethoxyethyl group, 5-methoxyhexyl group, 2-(trimethylsilyloxy)-2-hexyl group, halogenated methyl group, halogenated n-butyl group, halogenated n-pentyl group, halogenated nonyl group, phenyl group, benzyl group, halogenated phenyl group, n-pentyloxymethyl group, 1-ethoxy-2-methyl-propan-2-yl group, phenoxymethyl group, benzyloxymethyl group, p-chlorophenoxy methyl group, 2-phenylethyl group, benzyloxyethyl group, p-fluorophenoxymethyl group, phenylacetylenyl group, m-chlorophenoxymethyl group, m-trifluoromethylphenoxymethyl group, 1-butyl-cyclopropyl group, 3-ethyl-cyclopentyl group, benzothiophenon-5-yl group, 2-octenyl group, 3-methoxycarbonylpropyl group, and vinyl group.

7. The derivative according to claim 1, wherein the derivative is selected from the group consisting of

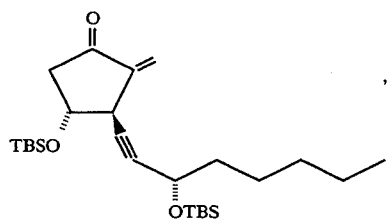

-continued

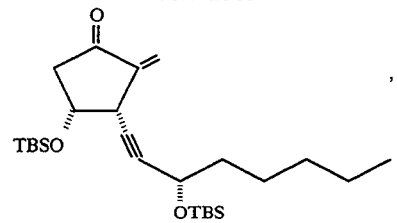

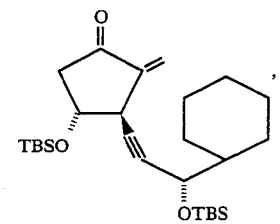

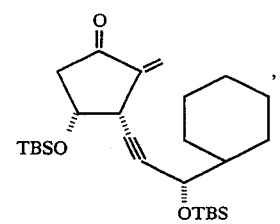

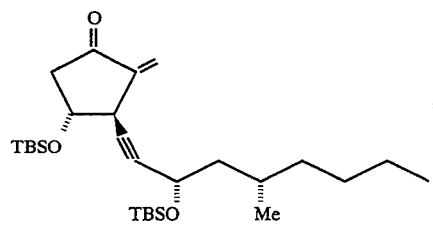

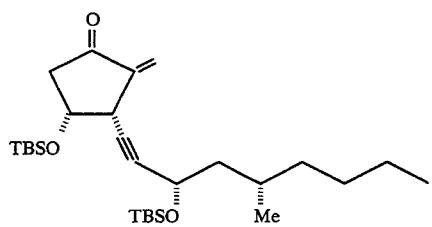

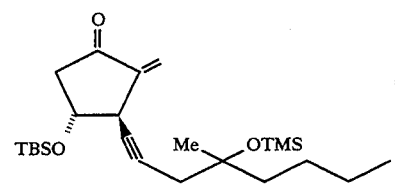

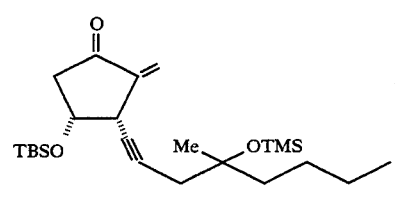

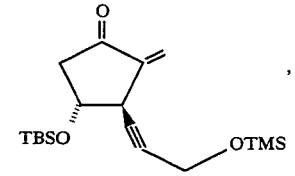

-continued

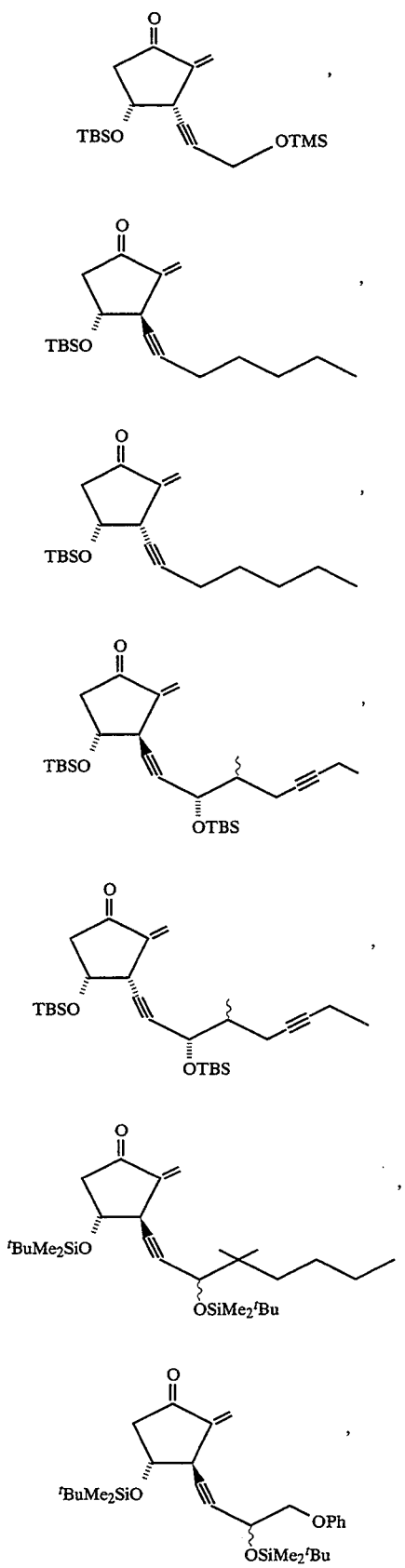

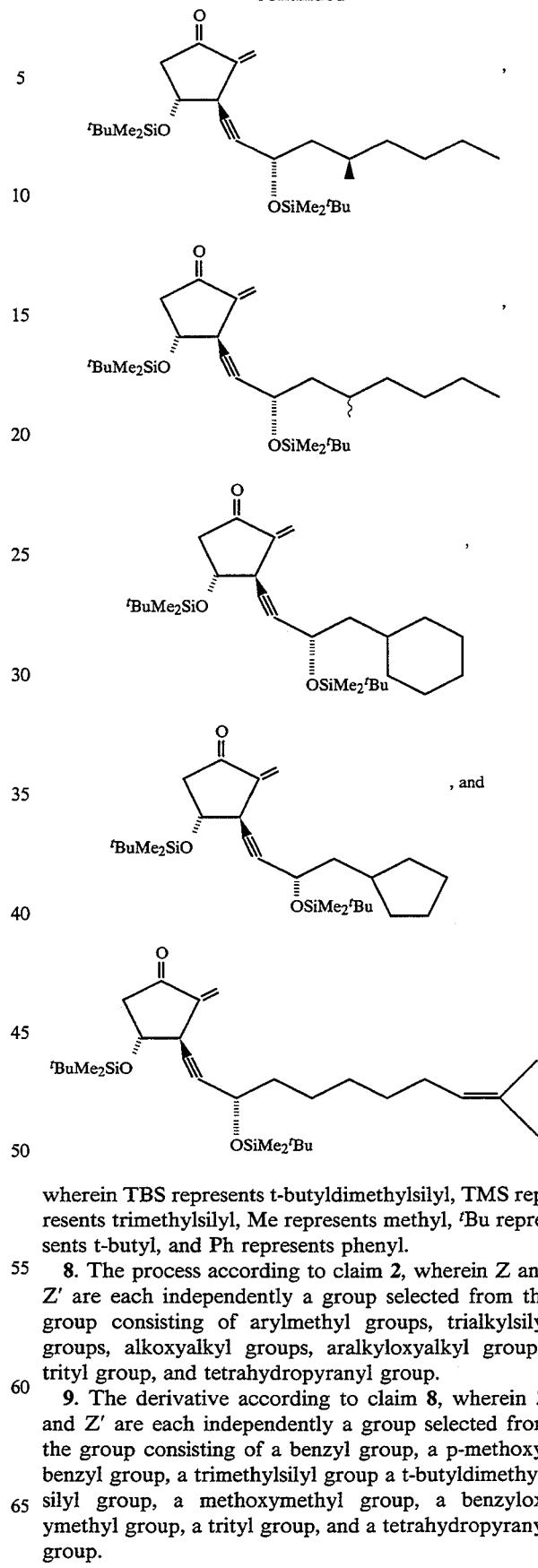

wherein TBS represents t-butyldimethylsilyl, TMS represents trimethylsilyl, Me represents methyl, ᵗBu represents t-butyl, and Ph represents phenyl.

8. The process according to claim 2, wherein Z and Z' are each independently a group selected from the group consisting of arylmethyl groups, trialkylsilyl groups, alkoxyalkyl groups, aralkyloxyalkyl groups, trityl group, and tetrahydropyranyl group.

9. The derivative according to claim 8, wherein Z and Z' are each independently a group selected from the group consisting of a benzyl group, a p-methoxybenzyl group, a trimethylsilyl group a t-butyldimethylsilyl group, a methoxymethyl group, a benzyloxymethyl group, a trityl group, and a tetrahydropyranyl group.

10. The derivative according to claim 9, wherein Z and Z' each independently represent a t-butyldimethylsilyl group or a trimethylsilyl group.

11. The derivative according to claim 2, wherein $R^2$ is selected from the group consisting of a methyl group, ethyl group, n-propyl group, i-propyl group, n-butyl group, i-butyl group, t-butyl group, amyl group, hexyl group, heptyl group, octyl group, nonyl group, decyl group, 2-methylhexyl group, 2-hexyl group, cyclopentyl group, cyclohexyl group, cyclohexylmethyl group, hexa-4-in-2-yl group, hept-4-in-2-yl group, 2,6-dimethyl-hept-5-en-1-yl group, pent-1-en-1-yl group, pent-2-en-1-yl group, hex-1-en-2-yl group, 3-ethoxy-2-methyl-propan-2-yl group, ethoxyethyl group, 5-methoxyhexyl group, 2-(trimethylsilyloxy)-2-hexyl group, halogenated methyl group, halogenated n-butyl group, halogenated n-pentyl group, halogenated nonyl group, phenyl group, benzyl group, halogenated phenyl group, n-pentyloxymethyl group, 1-ethoxy-2-methyl-propan-2-yl group, phenoxymethyl group, benzyloxymethyl group, p-chlorophenoxy methyl group, 2-phenylethyl group, benzyloxyethyl group, p-fluorophenoxymethyl group, phenylacetylenyl group, m-chlorophenoxymethyl group, m-trifluoromethylphenoxymethyl group, 1-butyl-cyclopropyl group, 3-ethyl-cyclopentyl group, benzothiophenon-5-yl group, 2-octenyl group, 3-methoxycarbonylpropyl group, and vinyl group.

12. The process according to claim 2, wherein said organoaluminum compound is used in an amount of 0.5 to 4 equivalents for said α-aminomethylcyclopentenone.

13. The process according to claim 2, wherein said organoaluminum compound is used in an amount of 0.8 to 2 equivalents for said α-aminomethylcyclopentenone.

14. The process according to claim 2, wherein said reaction is carried out in an organic solvent selected from the group consisting of tetrahydrofuran, hexane, pantane, benzene, toluene, and diethyl ether.

15. The process according to claim 2, wherein said reaction is carried out at a temperature within the range of −20° to 60° C.

* * * * *